US008932058B2

(12) United States Patent
Fisker et al.

(10) Patent No.: US 8,932,058 B2
(45) Date of Patent: Jan. 13, 2015

(54) IMPRESSION SCANNING FOR MANUFACTURING OF DENTAL RESTORATIONS

(75) Inventors: Rune Fisker, Virum (DK); Nikolaj Deichmann, Copenhagen (DK); Tais Clausen, Copenhagen (DK); Brieuc Gilles, Copenhagen (DK)

(73) Assignee: 3Shape A/S, Copenhagen (DK)

( * ) Notice: Subject to any disclaimer, the term of this patent is extended or adjusted under 35 U.S.C. 154(b) by 1779 days.

(21) Appl. No.: 12/095,154

(22) PCT Filed: Nov. 30, 2006

(86) PCT No.: PCT/DK2006/000678
§ 371 (c)(1),
(2), (4) Date: Oct. 13, 2008

(87) PCT Pub. No.: WO2007/062658
PCT Pub. Date: Jun. 7, 2007

(65) Prior Publication Data
US 2009/0220916 A1 Sep. 3, 2009

(30) Foreign Application Priority Data

Nov. 30, 2005 (DK) .................................. 2006 01693
Feb. 23, 2006 (DK) .................................. 2006 00259

(51) Int. Cl.
*A61C 8/00* (2006.01)
*A61C 19/04* (2006.01)
*A61C 9/00* (2006.01)
*A61B 6/00* (2006.01)

(52) U.S. Cl.
CPC . *A61C 19/04* (2013.01); *A61C 9/00* (2013.01); *A61C 9/0053* (2013.01); *A61C 9/002* (2013.01); *A61B 6/506* (2013.01)
USPC ........................................................ 433/173

(58) Field of Classification Search
USPC .......................... 433/172, 173, 196, 213, 214; 264/16–20; 700/98
See application file for complete search history.

(56) References Cited

U.S. PATENT DOCUMENTS

| | | |
|---|---|---|
| 5,338,198 A | 8/1994 | Wu et al. |
| 5,725,376 A | 3/1998 | Poirier et al. |
| 5,885,078 A | 3/1999 | Cagna et al. |

(Continued)

FOREIGN PATENT DOCUMENTS

WO WO-2006007855 A1 1/2006

OTHER PUBLICATIONS

Besl et al., "A Method for Registration of 3-D Shapes." IEEE Trans. Pattern Anal. Machine Intel. Feb. 1992 (vol. 14, No. 2) pp. 239-256.

(Continued)

*Primary Examiner* — Sunil K Singh
(74) *Attorney, Agent, or Firm* — Buchanan Ingersoll & Rooney PC

(57) ABSTRACT

The present invention relates to a method for obtaining an accurate three-dimensional model of a dental impression, said method comprising the steps of, scanning at least a part of an upper jaw impression and/or a lower jaw impression, obtaining an impression scan, evaluating the quality of the impression scan, and use the impression scan to obtain a three-dimensional model, thereby obtaining an accurate three-dimensional model of the dental impression.

17 Claims, 20 Drawing Sheets

(56) References Cited

U.S. PATENT DOCUMENTS

| | | | |
|---|---|---|---|
| 6,227,851 B1 * | 5/2001 | Chishti et al. | 433/24 |
| 6,540,514 B1 * | 4/2003 | Falk et al. | 433/173 |
| 6,579,095 B2 | 6/2003 | Marshall et al. | |
| 6,788,986 B1 * | 9/2004 | Traber et al. | 700/98 |
| 6,790,040 B2 | 9/2004 | Amber et al. | |
| 2002/0006217 A1 | 1/2002 | Rubbert et al. | |
| 2002/0039717 A1 * | 4/2002 | Amber et al. | 433/172 |
| 2004/0133293 A1 | 7/2004 | Durbin et al. | |

OTHER PUBLICATIONS

Curless et al., "Better Optical Triangulation Through Spacetime Analysis", 1995 5th International Conference on Computer Vision, Boston, MA Jun. 20-23, 1995.

European Search Report issued in corresponding European Application No. 11155407.7, dated Jan. 26, 2012.

\* cited by examiner

IMPRESSION SCANNING FOR MANUFACTURING OF DENTAL RESTORATIONS

The present invention relates to a system and a method for creating a three-dimensional model of the teeth and bite by scanning and aligning dental impressions.

All patent and non-patent references cited in the application, or in the present application, are also hereby incorporated by reference in their entirety.

BACKGROUND OF INVENTION

The present invention is related to the field of manufacturing of dental restorations such as crowns, bridges, abutments and implants. When a patient requires a dental restoration the dentist will prepare the teeth e.g. a damage tooth is grinded down to make a preparation where the crown is glued onto. An alternative treatment is to insert implants (titanium screws) into the jaw of the patient and mount crowns or bridges on the implants. After preparing the teeth or inserting an implant the dentist normally makes an impression of the upper jaw, the lower jaw and a bite registration or a single impression in a double-sided tray (also known as triple trays).

The impressions are sent to the dental technicians who actually manufacture the restorations e.g. the bridge. The first step to manufacture the restoration is traditionally to cast the upper and lower dental models from impressions of the upper and the lower jaw, respectively. FIG. 1a and FIG. 8 shows a dental model and a impression, respectively. The models are usually made of gypsum and often aligned in a dental articulator using the bite registration. The articulator simulates the real bite and chewing motion. The dental technician builds up the dental restoration inside the articulator to ensure a nice visual appearance and bite functionality. A proper alignment of the cast in the articulator is crucial for the final restoration.

CAD technology for manufacturing dental restoration is rapidly expanding improving quality, reducing cost and facilitating the possibility to manufacture in attractive materials otherwise not available. The first step in the CAD manufacturing process is to create a 3-dimensional model of the patient's teeth. This is traditionally done by 3D scanning one or both of the dental gypsum models. The 3-dimensional replicas of the teeth are imported into a CAD program, where the entire dental restoration or a bridge substructure is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

In an ideal 3D scanner and dental CAD/CAM solution the dental laboratory or dentist would not need to make a gypsum model from the impression but rather scan the impression directly. This would make the handling easier and less costly. Also the restoration would be more accurate as the impression geometry is more accurate than a sectioned gypsum copy of this. Even if an impression scan could be done with CT or MR scanning equipment such scanners are prohibitively expensive and do not provide the required accuracy. Optical scanners such as laser or white light 3D scanners are on the contrary less costly and provide a higher accuracy and detail level. The problem with optical surface scanners is that these typically cannot efficiently scan the narrow cavities of a dental impression. Typically the scans would lack data or be less accurate in the deep narrow parts of the impression.

An alternative to impression scanners is direct in-the-mouth scanners. However impression scans have a clear number of advantages compared to in-the-mouth scanners including no mandatory equipment investment at dentist clinic, virtually no training for impression taking, shorter chair time, a physical model can always be poured in case of scanning problems or used as physical reference, low accuracy for in the mouth scanners, no powdering of the patient mouth necessary, and significantly reduced difficulties in capturing the antagonist and larger areas and contrary to in-the-mouth scan the impression has the margin line clearly visible.

SUMMARY OF INVENTION

If an impression is scanned instead of a gypsum model the traditional dental model might not be made at the laboratory. If a traditional dental model would still be needed by the dental laboratory or dentist to check or modify the fit and design of the manufactured restoration such a model could still be provided from the impression scan by inverting the data and adding a virtual base or other features and then manufacturing this model with suitable 3D manufacturing equipment.

The present invention provides a solution for scanning the impressions directly thereby avoiding the time consuming and costly need for creating the gypsum cast, still obtaining the required accuracy of the final restoration. Accordingly, the invention relates to a method for obtaining an accurate three-dimensional computer model of a dental impression, said method comprising the steps of:
1) scanning at least a part of an upper jaw impression and/or a lower jaw impression, obtaining an impression scan,
2) evaluating the quality of the impression scan, and
3) if the quality does not allow for an accurate three-dimensional model of the dental impression, then
    filling one or more cavities of the dental impression with filling material to obtain a model of said cavities, and scanning said model to obtain a model scan, and
    aligning and combining said model scan and impression scan thereby obtaining a three-dimensional model, and/or
    rescanning one or more areas of interest of the dental impression, and
    aligning and combining said area of interest scan and impression scan thereby obtaining a three-dimensional model, or,
4) if the quality does allow for an accurate three-dimensional model of the dental impression, then
    use the impression scan to obtain a three-dimensional model,
thereby obtaining an accurate three-dimensional model of the dental impression.

In another aspect the invention relates to method for obtaining a three-dimensional model of a dental impression, wherein the alignment of the scans to obtain a correct bite is provided. Accordingly, the invention further relates to a method for obtaining a three-dimensional model of a dental impression, said method comprising the steps of:
    scanning the upper jaw impression and the lower jaw impression of a double sided impression obtaining a scan of the double sided impression,
    aligning the upper jaw impression scan and the lower jaw impression scan of the double sided impression,
    thereby obtaining a three-dimensional model of the dental impression.

It is clear that the two methods may be combined so that the scanning of the single sided impression may be conducted by the method for obtaining an accurate three-dimensional computer model of the single sided dental impression.

In a third aspect the invention relates to a method of evaluating the quality of an impression and/or a preparation, comprising the following steps:
   a. obtaining a three-dimensional computer model of said impression and/or prepation to be evaluated,
   b. evaluating the said impression and/or preparation based on the three-dimensional model.

By such an evaluation significant cost and/or strain may be saved by allowing fast feedback while the patient is still at the dentist office. It is clear that especially in combination with the other aspects of the invention such evaluation may provide valuable information to the dentist.

In a fourth aspect the invention relates to a method of obtaining a three-dimensional model comprising at least one tooth and neighbouring tissue(s) comprising the following steps:
   a. scanning at least a part of an upper jaw impression and/or a lower jaw impression and/or a double-sided impression, obtaining an impression scan,
   b. using at least one impression scan to obtain a three-dimensional pre-model,
aligning said three-dimensional pre-model with at least a part of a CT and/or MR and/or X-ray scan obtaining a new three-dimensional model. In this aspect the invention is particularly suitable for designing drill guides.

In a fifth aspect of the invention relates to a method of manufacturing at least one part of a tooth crown comprising the following steps:
   a. obtaining a three-dimensional model by scanning at least part of a dental impression comprising information about the site in which the crown is to be located,
   b. performing a CAD design of the at least one part of a tooth crown in and/or relative to said three-dimensional model obtaining a computerized model of the at least one part of a tooth crown,
   c. manufacturing said full or complete crown from at least part of the obtained computerized model.

In this way at least a part of the work performed manually today may be performed by the way of electronically guided manufacturing equipment providing the potential for lower cost and higher accuracy.

In a sixth aspect the invention relates to a method of obtaining orientation and localization of at least one dental implant comprising the following steps:
   a. obtaining an impression comprising at least one fixated impression abutment corresponding to said at least one dental implant(s) and/or
      obtaining an impression comprising at least one fixated impression abutment corresponding to said at least one dental implant(s) on which is mounted a scan implant/analog and/or
      a positive model of at least a part of an upper jaw and/or a lower jaw comprising at least one model implant/analog, with orientation and localization corresponding to the orientation and localization of the dental implant(s), and/or
      a positive model of at least a part of an upper jaw and/or a lower jaw comprising at least one model implant/analog, with orientation and localization corresponding to the orientation and localization of the dental implant(s) on which is mounted a scanning abutment,
   b. obtaining pre-determined information of the shape of the impression abutment and/or scan implant/analog and/or model implant/analog and/or scanning abutment,
   c. scanning at least a part of said impression, wherein said part comprises the at least one impression abutment and/or scan implant/analog thereby obtaining scan data, and/or
      scanning at least a part of said positive model wherein said part comprises at least one model implant/analog and/or scan abutment, thereby obtaining scan data,
   determining the orientation and localization of the dental implant based on said pre-determined information and said scan data. This aspect of the invention enables CAD design, such as of a prosthetic tooth connected to said implant as this requires the exact location orientation of the implant.

In a seventh aspect the invention relates to a method of manufacturing a dental model of at least a part of an upper jaw and/or a lower jaw comprising the steps of:
   a. obtaining a three-dimensional model of at least the said part of the upper jaw and/or a lower jaw by either impression scanning, in-the mouth scanning, CT, MR or x-ray scans, scanning of a positive model or a combination thereof,
manufacturing a dental model from the obtained three-dimensional model. Such a method of manufacturing dental models from a obtained data may enable easier storage of dental models in that only the data is stores and a physical model may be produced if needed. Such models may also be utilized to omit the necessity to ship impressions and/or models between sites such as place of manufacturing abutments and a place of handling models and/or scanning.

In an eighth aspect the invention relates to a computer program product including a computer readable medium, said computer readable medium having a computer program stored thereon, said program comprising instructions for conducting the steps of the other aspects of the invention.

In a ninth aspect the invention relates to a system for producing a three-dimensional computer model and/or at least one part of a tooth crown/bridge, said system including computer readable memory having one or more computer instructions stored thereon, said instructions comprising instructions for conducting the steps of the other aspects of the invention.

In a tenth aspect the invention relates to a tray suitable for obtaining a single or double sided dental impression characterized in that said tray further comprises fixture means suitable for holding the tray in a three-dimensional scanner. By this aspect the need for additional fixation means in the scanner may be omitted and scanning process may by significantly simplified.

In a eleventh aspect the invention relates to a tray suitable for obtaining a double sided dental impression characterized in that said tray is mechanically stable by reinforcements by at least one of the following materials metal, steel, and fibre-composite. With such a reinforced tray it may be possible to omit the need for single sided impressions.

Furthermore, invention relates to a method for obtaining an accurate three-dimensional computer model of a dental impression, wherein the impression is scanned using one sensor, i.e. camera and light source, having an angle A between the light source and the camera, and afterward regions of interest are rescanned using another sensor, wherein for said other sensor there is an angle B between the light source and the camera, and said angle B is smaller than said angle A. Thereby it is possible to scan deeper cavities than it will be using only one scanner having the angle A. The invention may further comprise a step of determining the angle B based on the impression scan, before the rescan-step is performed. Preferable the angle B is less than 95% of angle A, less than 90% of angle A, less than 85% of angle A, less than 80% of angle A, less than 70% of angle A, less than 60% of angle A, less than 50% of angle A, less than 40% of angle A, less than 30% of angle A, less than 20% of angle A, less than 10% of angle A, less than 5% of angle A.

Finally, the invention relates to a method for obtaining an accurate three-dimensional computer model of a dental impression, said method comprising the steps of:
1) scanning at least a part of an upper jaw impression and/or a lower jaw impression using a three-dimensional sensor having an angle A between the light source and the camera, obtaining an impression scan,
2) evaluating the quality of the impression scan, and
3) if the quality does not allow for an accurate three-dimensional model of the dental impression, then
   selecting another three-dimensional sensor having an angle B between the light source and the camera, wherein the angle B is smaller than the angle A,
   rescanning one or more areas of interest of the dental impression using said selected sensor, and
   aligning and combining said area of interest scan and impression scan thereby obtaining a three-dimensional model, or,
4) if the quality does allow for an accurate three-dimensional model of the dental impression, then
   use the impression scan to obtain a three-dimensional model,
thereby obtaining an accurate three-dimensional model of the dental impression.

DESCRIPTION OF DRAWINGS

FIG. 9b shows the inverted scan of the scan of FIG. 9a.
FIG. 11b shows scan of the dies of FIG. 11a.
FIG. 19 3D printed model mounted in articulator.

DEFINITIONS

Figure 1A:
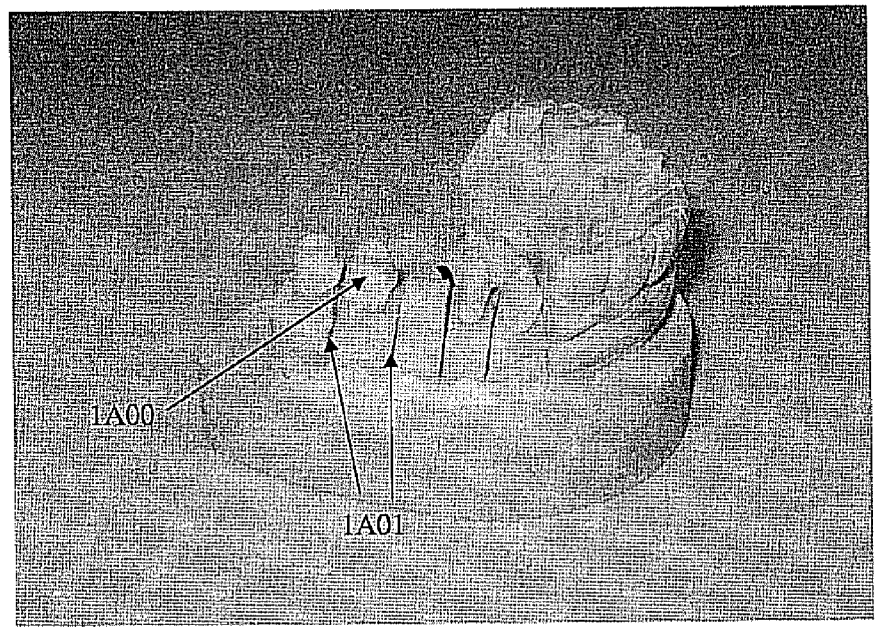
FIG. 1a: Dental gypsum model
Figure 1B:
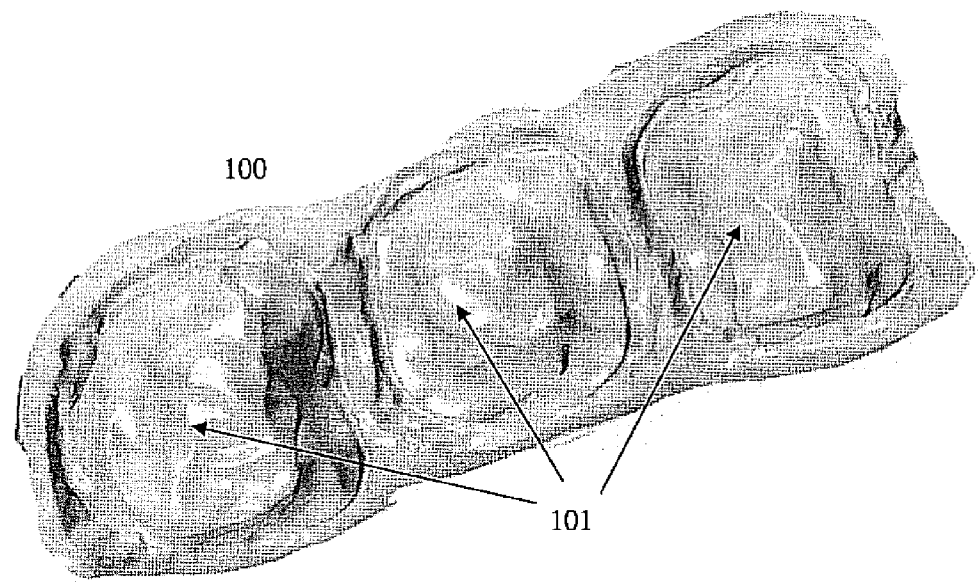
FIG. 1b: 3D scan of single side impression

Dental impression: a negative impression of the teeth preferably made in a tray.
Dental model: a positive replica of the teeth made from the dental impression.

DETAILED DESCRIPTION OF THE INVENTION

The objective of the invention is an improved scanning and alignment method for scanning dental impressions used as input for CAD manufacturing of dental restorations avoiding the costly and time consuming manufacturing of dental gypsum models. Impression scanning will also improve quality since the traditional casting process and dental model segmentation introduces errors. Furthermore, impression scanning will not increase chair time for patients at the dentist, there is no mandatory entry cost for the dentist, no education of the dentist is required and the overall manufacturing time is reduced thereby improving patient satisfaction and potentially avoiding temporary restorations.

Accurate Three-Dimensional Model

The scanning of dental impressions by optical 3D scanners is very challenging mostly due to a lack of visibility in cavities. A traditional 3D scan will thus result in a lack of coverage, i.e. the 3D scan may have holes or missing areas that have not been scanned. The present invention provides a solution to that problem. As described above, one solution may be to rescan, optionally using a different scanner and/or a different scanner setting, one or more regions of interest of the impression, to provide a scan having a better quality, such as fewer holes, or no holes in the region of interest. Thus the term scan "quality" means quality in relation to coverage and accuracy of the scan. Insufficient coverage might be automatically detected by triangulation of the surface and then locating the holes on the surface. A good quality requires no holes or only very few holes in the regions of interest. If any holes are accepted, the position of such holes may not interfere with the production of an accurate three-dimensional model. In practice this means that holes must not be in the preparation area. The preparation area can be located based on manual selection or preferably automatically detected e.g. using feature detection. Examples of critical holes 1000 in the preparation area are shown in FIG. 10.

Furthermore, noise may lead to less accurate scans. Noise is a particular dominant problem when scanning into cavities like impressions, since the cavities creates significant amount of tracking and half occlusion noise. Half occlusion noise is described in details in Curless and Levoy (1995). Lack of accuracy due to noise 1001 is shown in FIG. 10. Half occlusion noise and coverage is the main limitation for practical use of impression scanning and determining whether a scan points is a noise point or a true point is very critical for the final quality of the dental restoration. Hence it is very critical to determine noise and coverage problems automatically. Noise points might be automatically detected using point quality derived from the laser tracking, surface orientation at capture, multiple cameras views, local surface statistics, surface curvature, shape statistics or reverse ray-tracing.

By the term "accurate three-dimensional model" is meant a model that possess such accuracy that it may be used directly for producing the dental restoration.

Another important quality evaluation that instantly can be derived from the scan is the quality of the impression and preparation, respectively. In fact low quality impressions and poor preparations created by the dentist are two of the largest quality issues for the final restoration. However the quality of the impression and preparation can be evaluated based on the scan e.g. by under cut detection, air bubble detection, noise level, impression material evaluation, shape evaluation or geometrical measurements. The result of the evaluation can be shown visually on the 3D scan to guide the dentist to improve the impression or preparation.

Particular if the scan is performed directly in the dentist clinic then an impression and preparation quality evaluation might potentially lead to taking a new impression or improving the preparation. Preferably, a fast scanner, such as the 3Shape D250 scanner, is employed so that the evaluation may be performed while the patient is waiting. This could significantly improve restoration quality and/or reduce patient discomfort and cost by eliminating the delay and effort involved in a second consultation to retake an impression.

Other types of quality influencing the final result of the restoration might also be evaluated.

The quality evaluations described might also be performed on other types of scans of the mouth region such as traditional 3D scans of gypsum models, directly in the mouth scans, CT, MR or x-ray scans.

Scanning into cavities like a dental impression is a challenging problem using a price competitive structured light scanner. The problem originates from the fundamental construction with a light source projection a pattern onto the object where one or more sensors acquire images of the projected pattern. To perform the 3D reconstruction an angle of typically 20-30 degrees between light source and sensor is required. The required angle and the fact that the sensor and laser need to see the same point on the surface at the same time to make a 3D reconstruction strongly limits the scanners ability to scan cavities. To achieve the optimal result the actual viewpoint becomes crucial. Scanners with at least 3 axis, such as the 3Shape D200, D250 or D300 scanner, can reorient the object in 3D and hence change the relative viewpoint. Adaptively changing the view point and scanning sequence to match the individual object can be applied to obtain coverage in difficult dental impressions as described in WO 2006/007855.

In one embodiment the quality of the impression scan is improved by selecting or automatically detecting one or more regions or interest and rescan such regions of interest. The rescanning may be conducted using a scanner and/or scanner setting optimised to the specific region of interest.

Missing areas can be rescanned by detecting these in the initial 3D dataset and then calculating the optimal mechanical positioning of the impression or the 3D sensor with regards to their relative position in order to cover the missing areas in an additional automatic scanning session. The optimization function takes into consideration the exact position of the detected hole and also the surrounding impression geometry that might occlude the view of the light source and/or cameras.

The rescan could also be performed by utilizing an additional 3D sensor (camera and light source) or one or more extra cameras in the scanner. Such additional sensor should have a smaller angle between light source and camera and would thus be able to look into cavities with a higher debt to width ratio. In such embodiment a camera and light source combination with a higher angle between light source and camera could be used to make a first scan and then an additional camera or light source with a lower angle with respect to the light source/camera could be used to cover the deepest areas of the cavities.

The rescanning may also be conducted after having cut the impression to improve visibility. If the required cuts destroy areas with needed information then the scans before and after cutting can be aligned and combined to form a complete 3D model. Typically the uncut scan will include the margin line area, which will then be cut away to create visibility into the deep cavities corresponding to leaving the impression of the top of the teeth remaining. However, the model may be cut one or more time to achieve accurate scanning. The model is scanned prior to each cut and the corresponding three-dimensional models may then be aligned either sequentially of simultaneously.

In another embodiment the problem of scanning into the cavities is solved by making a model of the cavity(ies) by filling a filling material into the cavity. Then the model of the cavite(ies) may be scanned, and the scan(s) aligned and combined with the impression scan. In one embodiment at least two cavities are filled, such as at least three cavities. The cavities may be neighbouring cavities or cavities separated by one or more un-filled cavities.

Figure 10A:
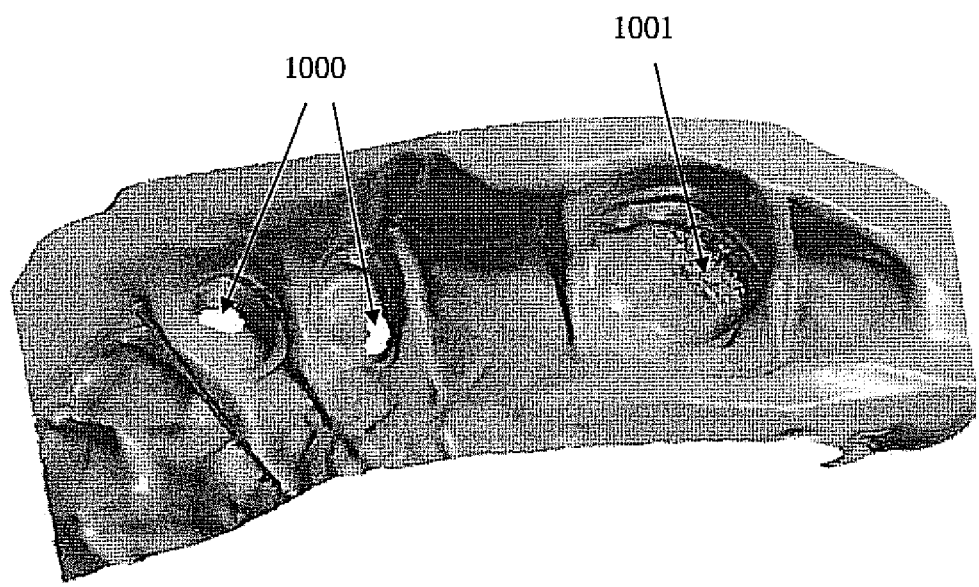
FIG. 10a shows a scan of the impression from FIG. 8 having a poor quality with little accuracy due to noise 1001 and holes 1000.
Figure 10B:
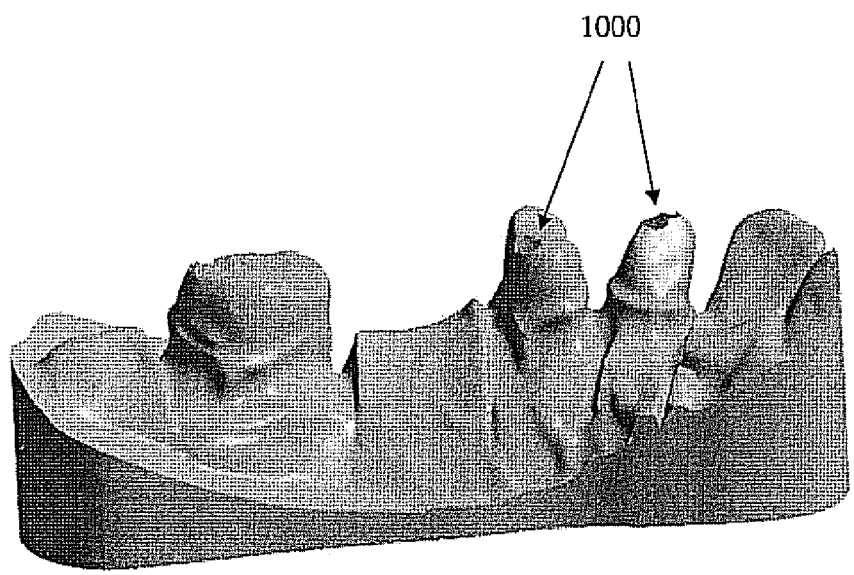
FIG. 10b shows the inverted scan of the scan of FIG. 10a showing the result of the noise and the holes.
Figure 10C:
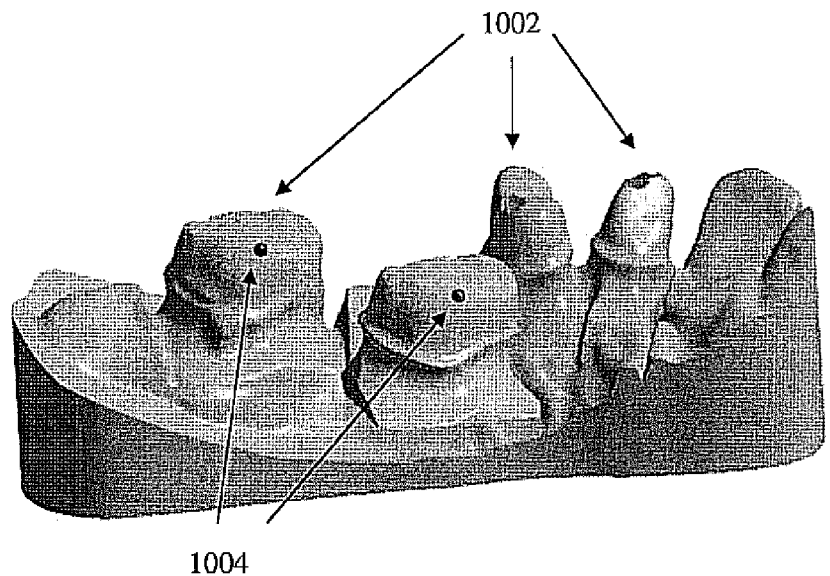
FIG. 10c shows example of alignment of scan of a single tooth (from FIG. 11b) with the inverted scan of FIG. 10b.
Figure 10D:
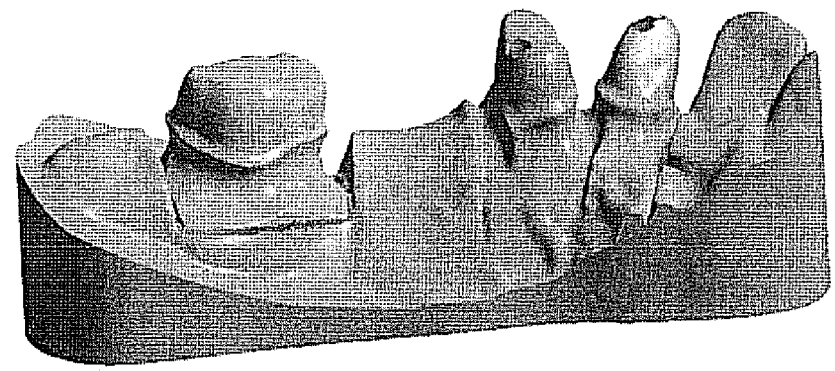
FIG. 10d shows the aligned bridge after first alignment done in FIG. 10c.
Figure 10E:
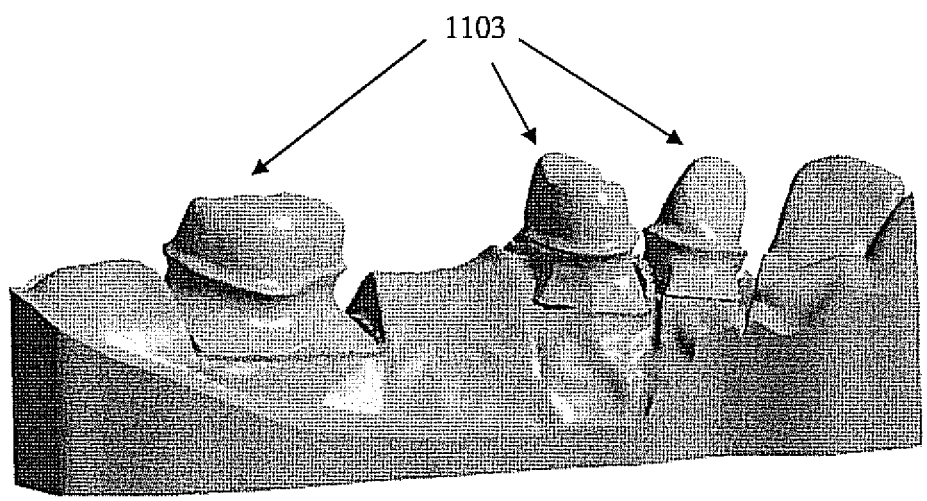
FIG. 10e shows the final aligned bridge after all alignments.
Figure 11A:
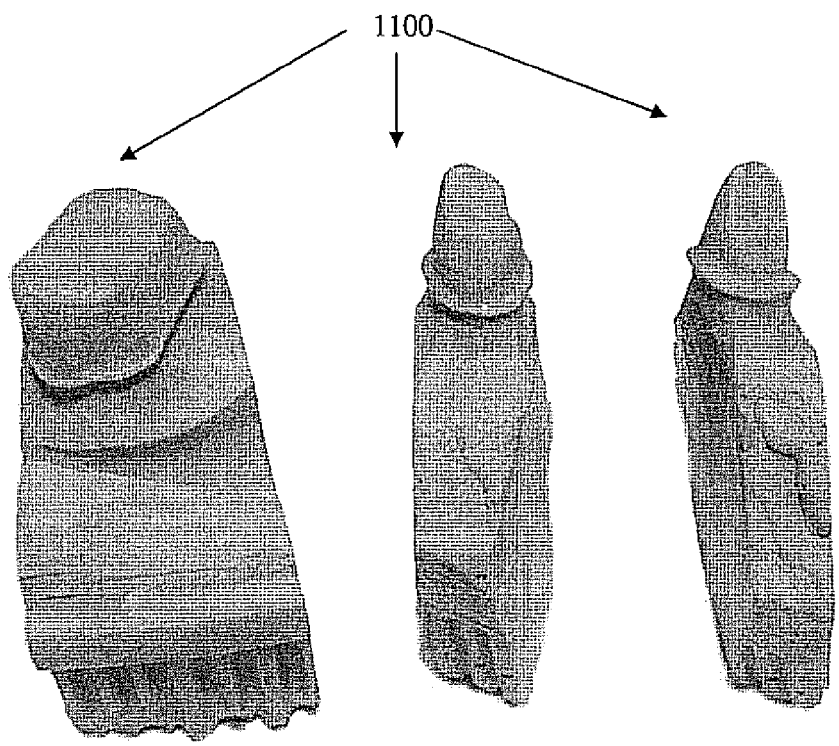
FIG. 11a shows dies of impression cavities from three different teeth.
Figure 11B:
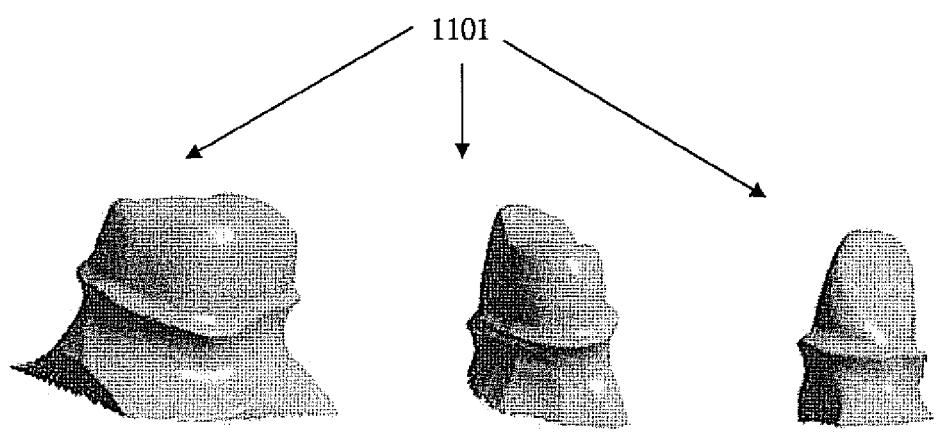
Figure 12:
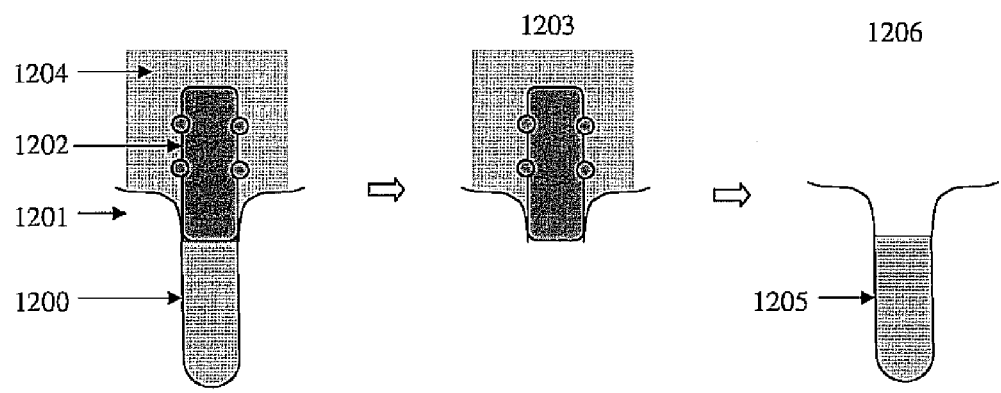
FIG. 12 Traditional transfer of implant position and orientation from patient mouth to dental model.
Figure 13:
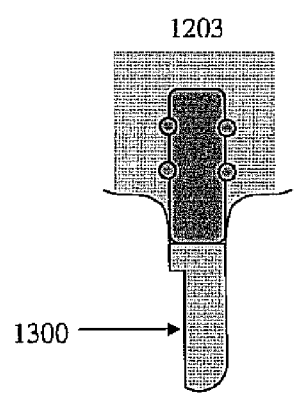
FIG. 13 Scan analog mounted in impression abutment to obtain position and orientation of implant.
Figure 14:
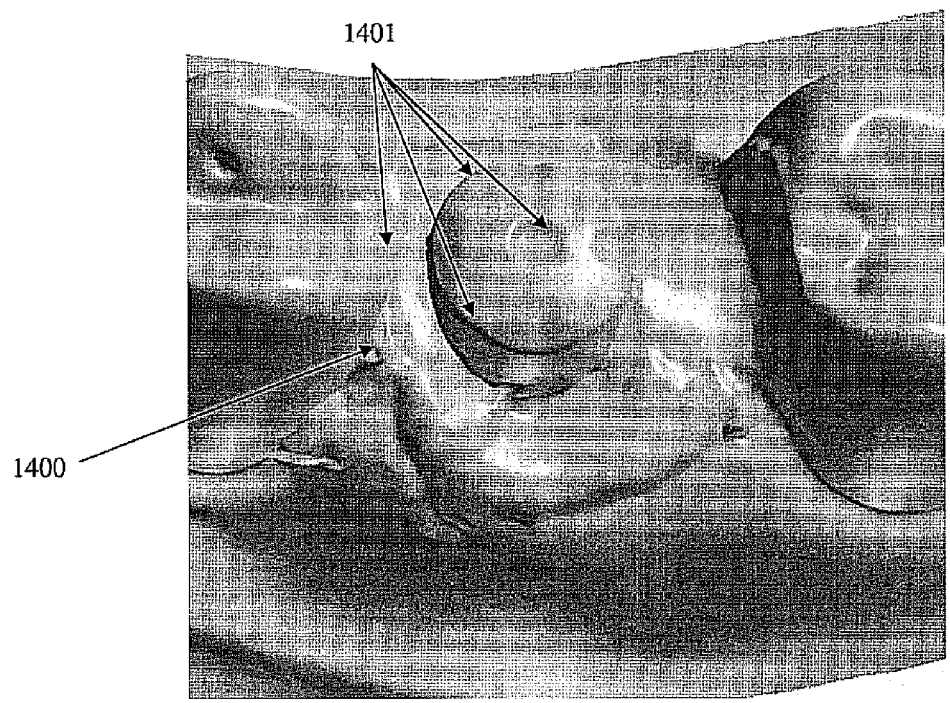
FIG. 14 Impression scan of Encoded Healing Abutment (EHA)
FIG. 15 Turning the impression (negative) to model (positive) by rotation and cutting away superfluous surface.

The process is illustrated in FIGS. 10a and 10b where 2 preparations are lacking coverage 1000 and one preparation has noise issues 1001 create quality problems. The models for 3 problematic preparations are then poured as separate gypsum models 1100 using the impression. These 3 "positive" models are then scanned 1200 without quality issues and the scans are aligned and merged 1103 into the corresponding preparations 1102 in the impression. The alignment might be performed by selecting corresponding points 1104 on the two scans followed by an ICP alignment (Besl and McKay, 1992). In yet another embodiment the problem of scanning into cavities is solved by combining rescanning of regions of interest and model scanning. In some embodiments it is preferred to provide models in that the models may be prepared manually and for example clearly include lines delining the tooth, so that the scan also includes the distinct lines.

The visual properties of the impression material are also very important for the scan quality. This is in particular true for a deep or thin tooth where inter reflections can create image tracking software problems and significant noise. Problems with half occlusion noise at the edge of occlusion can also create significant scanning artefacts, which might be removed by a reverse ray-tracing algorithm.

The aligned scan are combined, e.g. by replacing the impression scan parts with corresponding parts of the model scan or region of interest scan or both and merging the common surface of the scans. The alignment of the scans may be conducted as described below in relation to the three-dimensional model including bite information.

The method according to the invention may further include a step of pre-scanning the impression before the impression scan is conducted. By the information obtained from the pre-scan it is possible to adjust the scanner settings and scan sequence including motions for making more accurate impression scans or regions of interest scans.

Depending on the restoration to be made based on the accurate three-dimensional model the whole impression scan may be used to provide the model, or only a region of the impression scan may be used. Therefore, in one embodiment a region of the impression scan is defined before alignment, and in a further embodiment alignment is conducted only for said defined region. In one example the alignment is performed for at least two teeth, such as at least three teeth.

In general the reflectivity of the impression material should be as little as possible. In one embodiment the impression material is coated before scanning, such as coated with a non-reflective coating thereby improving the scanning quality. In another embodiment the impression itself is made from a material having a little or no reflective characteristics.

Alignment of upper jaw scan and lower jaw scan may be conducted by any suitable method. In one embodiment the alignment is conducted using CT-scans or MR-scans of the jaws. One advantage may be that such scans also include information of jaw and nerves. In another embodiment the alignment of upper jaw scan and lower jaw scan is conducted using a double-sided impression scan, for example as described below.

Of course CT-scans and MR-scans may be used for other alignment purposes if necessary. CT or MR scans might also be combined and/or aligned with impression scans, e.g. for design of drill guides for implants or simply to provide an improved three-dimensional model.

Three-Dimensional Model Including Bite Information

The basis for the scan is at least two dental impressions. One impression is a double sided impression that captures the upper, the lower jaw and the bite in one impression. Unfortunately the double trays may lack physical stability creating lower quality impressions and is not accepted by many dentists. To compensate for this problem at least one single side impression is also created, thereby mapping only the upper or lower jaw. The single sided impression is created in a traditional tray with very high physical stability providing high quality impression.

The possible quality problem with the double sided impressions can be solved by aligning and combining scans of the double sided impressions with one or two single sided impression scans. The accuracy requirement at the prepared teeth area is 20 microns where as the bite and the antagonist teeth only requires 50-100 microns. By applying the single sided scan at the prepared area and the double sided scan for the bite and antagonist teeth the accuracy demand will be fulfilled. Optionally an additional single sided scan is made of the antagonist side.

Figure 2:
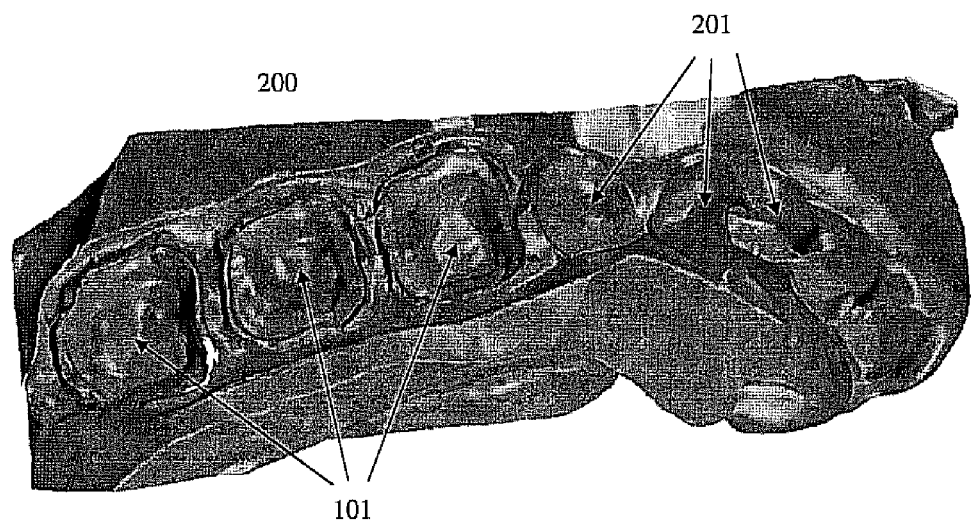
FIG. 2: 3D scan of upper part of double side impression
Figure 3:
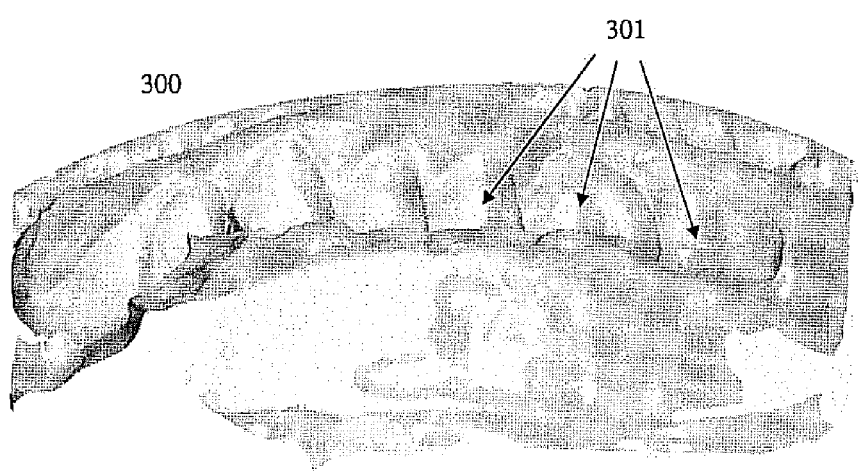
FIG. 3: 3D scan of lower part of double side impression
Figure 4:
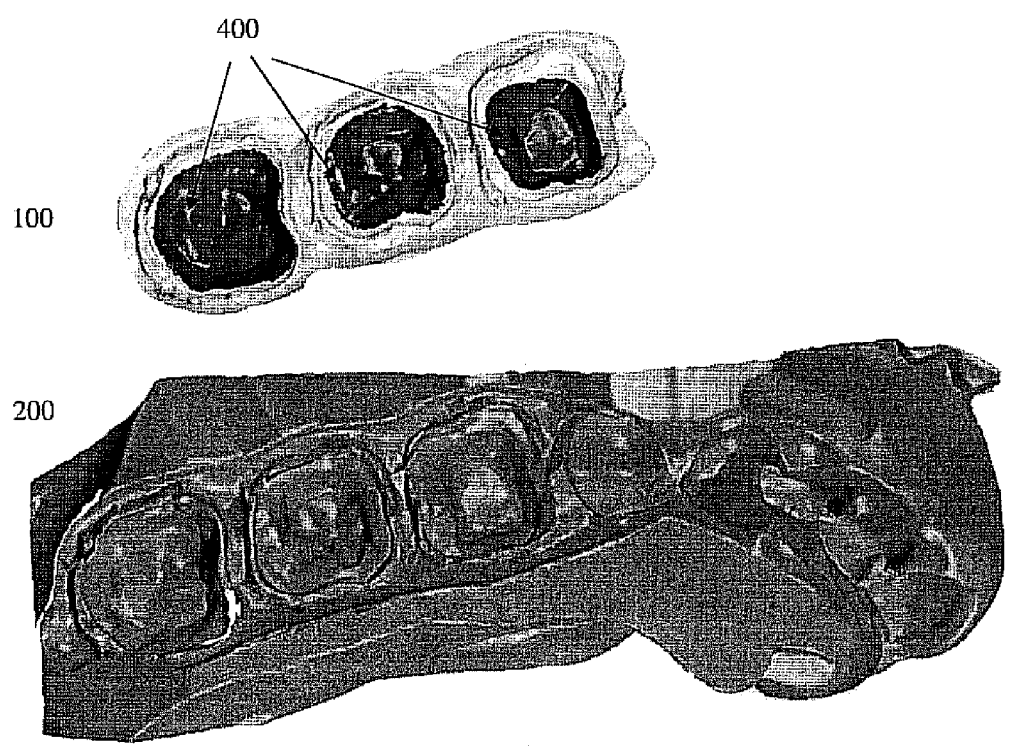
FIG. 4: Representative parts for alignment

The following scans need to be created in any order:
1. 3D scan 100 of single side impression prepared for the restoration, see FIG. 1a (optionally)
2. 3D scan 200 of upper side of double sided impression, see FIG. 2
3. 3D scan 300 of lower side of double sided impression, see FIG. 3
4. 3D scan of single side impression at antagonist side (optionally)

Note the prepared teeth 101, the normal unprepared neighbouring teeth 201 and the antagonist teeth 301.

Figure 5:
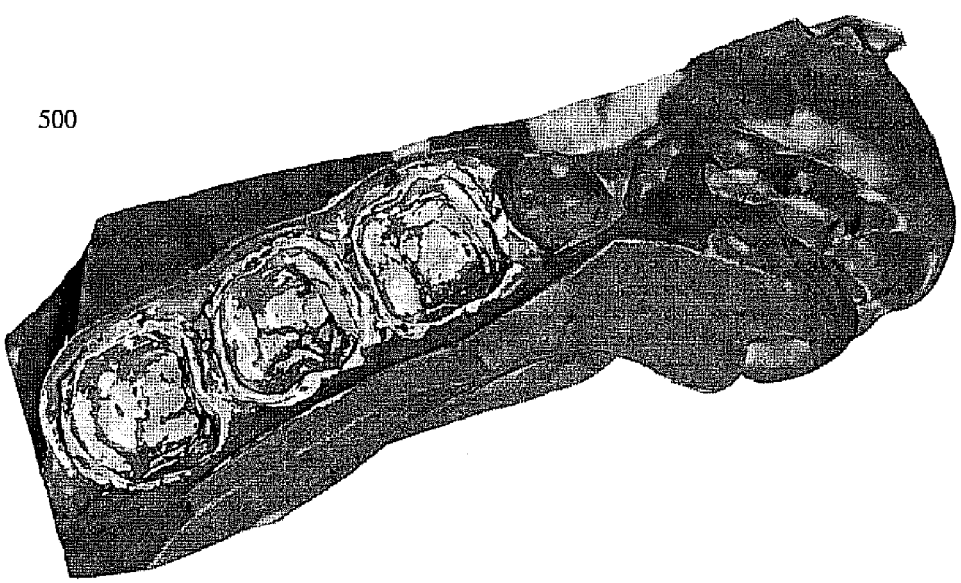
FIG. 5: Superimposed alignment of FIG. 4
FIG. 6: Representative parts for alignment
Figure 6:
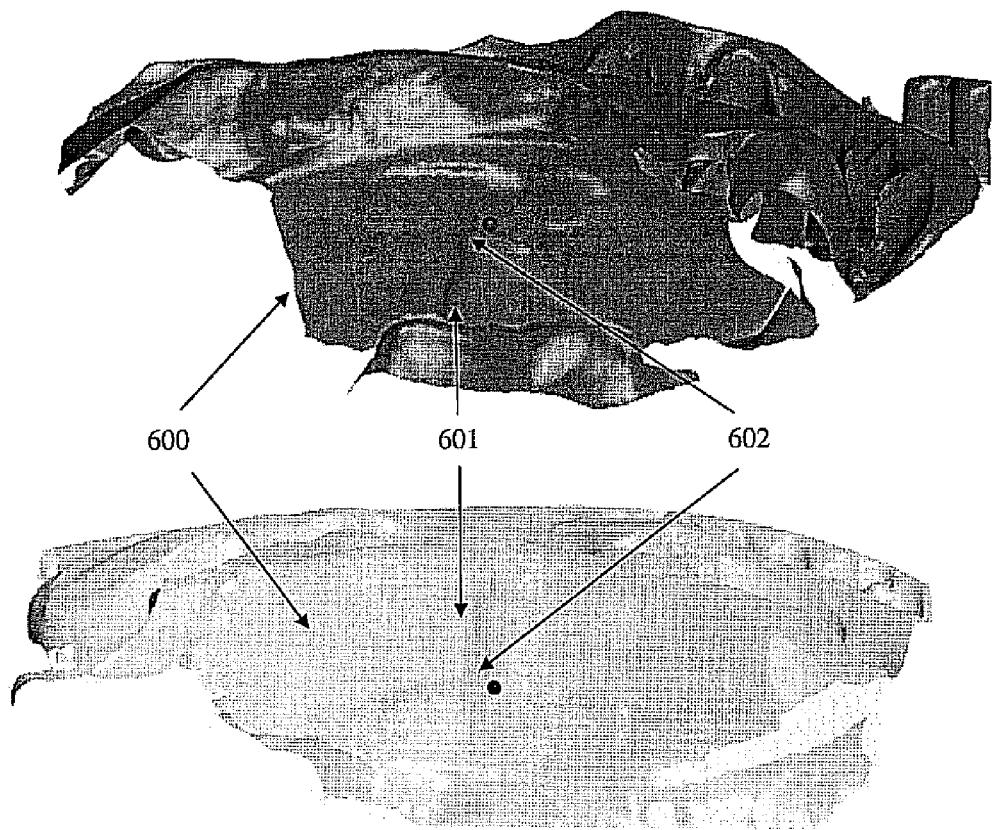

The next step after scanning is to perform a region-based alignment of the single impression scans 100 with the corresponding double sided scan 200. Unfortunately non-common data originating from the fact that the two impressions often differ outside the preparation line significantly complicates the alignment process. This is especially true because the operator will need to cut back the impression to create visibility for scanning deep teeth. In one embodiment of the invention a region 400 is defined where common high quality exists. The definition of the region can e.g. be performed by an operator or automatically by the computer. During the alignment process only the data in the regions are used. The alignment can be performed e.g. using the ICP algorithm (Besl & McKay, 1992). The superimposed result of the alignment is shown in FIG. 5.

Figure 7:
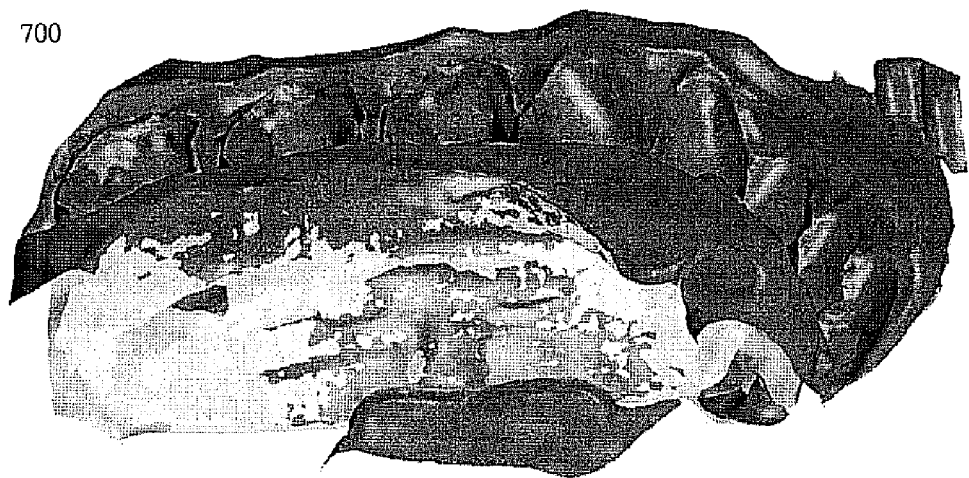
FIG. 7: Superimposed alignment of FIG. 6
Figure 8:
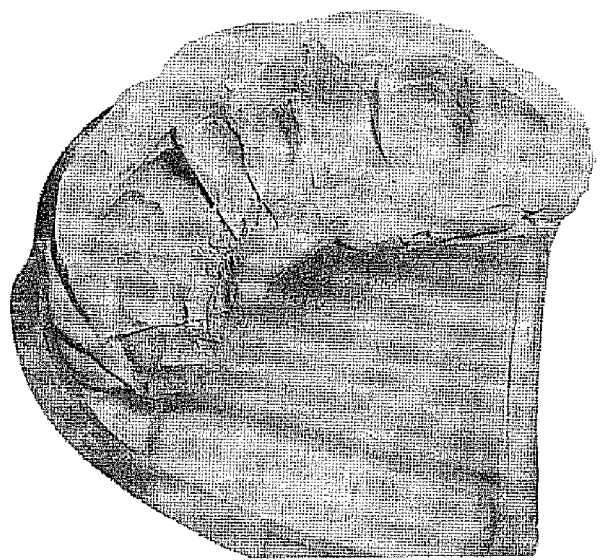
FIG. 8 shows an impression of teeth
Figure 9A:
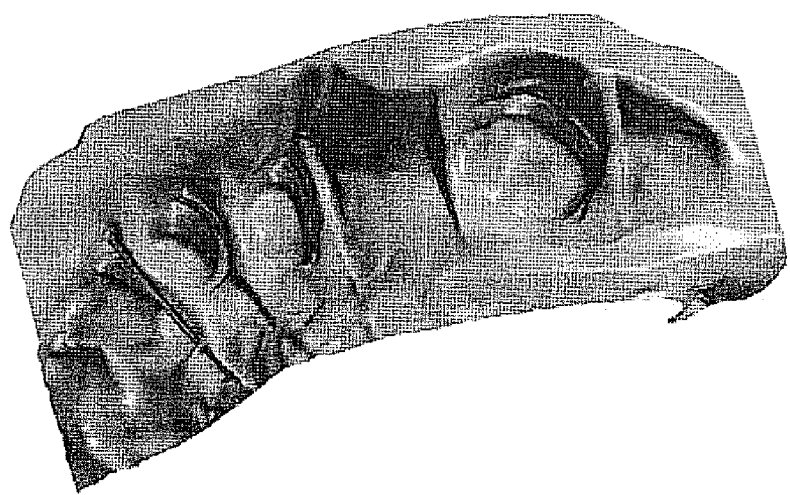
FIG. 9a shows a scan of the impression from FIG. 8 having good quality.
Figure 9B:
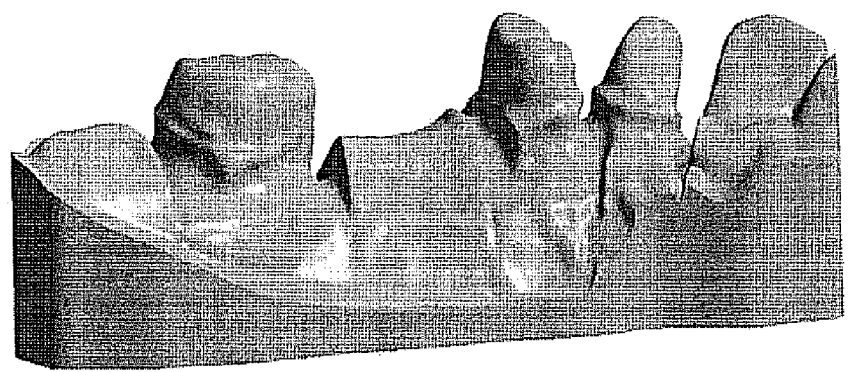
Figure 9C:
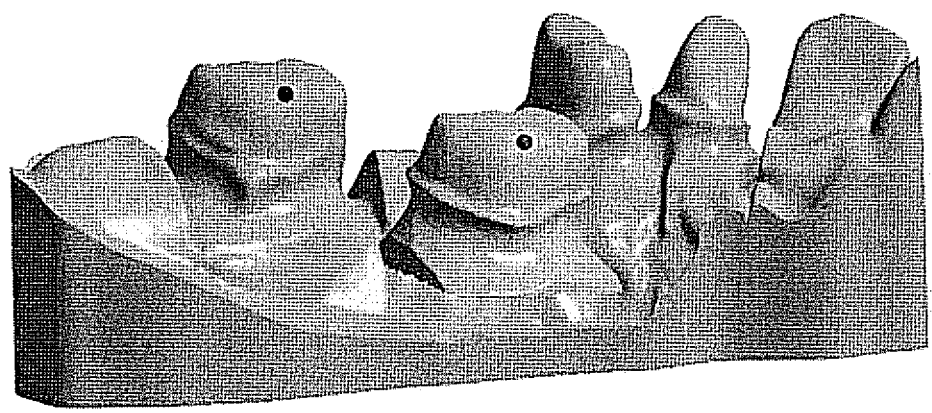
FIG. 9c shows example of alignment of scan of a single tooth (from FIG. 11b) with the inverted scan of FIG. 9b.
Figure 9D:
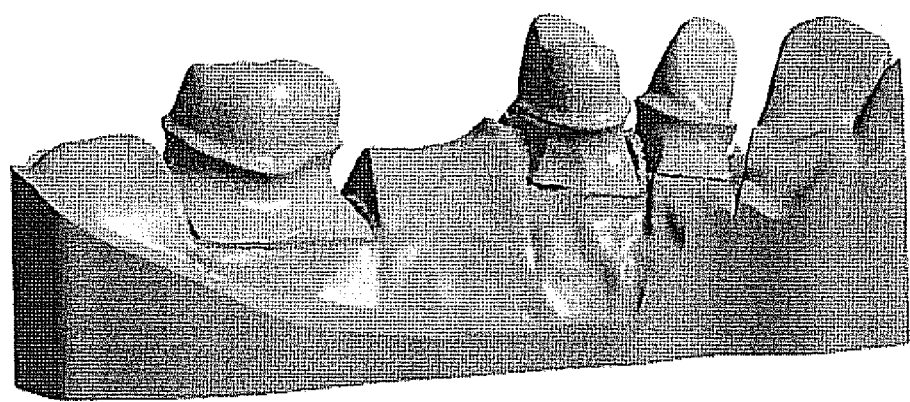
FIG. 9d shows the aligned bridge after first alignment done in FIG. 9c.

The alignment of the two double side impression scans requires a tray that facilitates scanning of common data such as vertical sides 600 of the tray and special alignment features e.g. a T-shape 601, dots or vertical lines. When common data exists the two scans can be aligned using a standard alignment algorithm such as ICP. The initialization for the alignment can e.g. be done by the computer or by the user selecting two corresponding points 602. The superimposed result of the alignment is shown in FIG. 7. The tray might be designed such that it fits directly into the scanner for easy handling. Furthermore, the tray may include a fixturing system for connecting directly to the scanner. The tray or impression might also include a horizontal eye line to be aligned with the eyes of the patient so that visual appearances of prosthetic tooth/teeth may be aligned with over facial features of the patient during the design. Obviously, such a tray may preferably be combined with any of the methods and systems described.

In another embodiment of the invention the double sided tray can be placed in a scanning fixture, which is included in the two scans. Only the fixture then needs to contain common data and alignment features. The impression may be turned automatically.

Finally the aligned scans are combined, e.g. by replacing the double sided scan with the corresponding part of the single sided scan and merging the common surface of the two double side scans.

Optionally a single sided scan can also be performed on the antagonist side and aligned and combined with the existing data in a similar procedure.

The development of double sided trays with improved properties such as physical stability and proper bite mapping may potentially make the single sided impression superfluous. In one embodiment, the double sided tray obtains increased stability by reinforcement, such as a metal, steel, and/or fibre-composite reinforcement. Obviously, such a tray may preferably be combined with the features of the tray described above and any of these trays are preferred when obtaining impressions in relation to any the methods and systems described in this document.

Although the text relating to three-dimensional models including bite information relates to scan of dental impressions, it is clear for the person skilled in the art that the same method and system may be used for scanning a dental model.

As described above, the single sided scans may be performed by the method for obtaining an accurate three-dimensional model of the dental impression.

In another aspect the invention relates to a computer program product including a computer readable medium, said computer readable medium having a computer program stored thereon, said program for producing a three-dimensional model of a dental impression comprising program code for conducting the steps of the method as defined above.

In a further aspect the invention relates to a system for producing a three-dimensional model, said system including computer readable memory having one or more computer instructions stored thereon, said instructions comprising Instructions for conducting the steps of the method as defined above.

Manufacturing of a Crown

Impression scanning becomes particular interesting in combination with CAD design of the full anatomical crowns followed by the manufacturing of the complete crown, both referred to as tooth crown. With such an approach there is no need for a model to complete the design and manufacturing. However, if the impression scan is only used for coping design then a model is still required to complete the design. The full crown might be designed with a suitable manufacturing process such as separating the designed crown into two or more layers where the inside layer corresponds to the coping and the outside layers is the ceramic. The coping can be manufactured using known equipment such as milling, machines, 3D wax printers or sintering machines. The outer layer might be manufactured by first manufacturing a copy in wax, plastic, polymers or other material that can melt e.g. using milling machines or 3D printers. This wax copy is then mounted on the coping and over pressing technologies such as Ivoclars Impress can be used to create the ceramic layer.

Implants

In another embodiment of the invention the dental restoration is implants 1200, which are typically titanium or zirconia "screws" that are inserted into the gingival 1201 and jaw bone. To perform the CAD design of the crown or bridge fitting on the implant it is required to locate the exact position and orientation of the implant from the impression scan.

Traditionally the position and orientation of the implant 1200 is transferred from the mouth of the patient to the dental model by the use of impression abutments 1202. In practice the transfer is performed by mounting impression abutments on the implants. A dental impression 1203 is then taken where the impression abutments are fixated in the impression material 1204 and the abutments are released form the implant. The impression 1203 including impression abutments 1202 is removed from the patient mouth. Then model implants/analogs 1205 are mounted on the impression abutments and the model 1206 is poured from the impression—typically in gypsum. The last step is to remove the impression 1203 and impression abutments 1202 when the model is hardened. In one embodiment of the invention the position and orientation of the implant is obtained by scanning the poured positive model wherein scanning abutments are mounted to facilitate easy determination of the position and orientation of the model implants/analogs, and thereby the position and orientation of the implants, from the scanning data. One method of determining said orientation and position from data obtained from the scanning abutment is to overlay the corresponding model data with CAD data of the shape of the scanning abutment. Here the scanning abutment may be identical to or different from the impression abutment.

In another embodiment of the invention the position and orientation of the implant is determined directly from the impression by scanning the impression abutment 1202 mounted in the impression 1203 and then use the knowledge of its 3D shape and dimensions e.g. CAD model. In practice the position and orientation might be obtained by features extraction or alignment a CAD of the impression abutment to the corresponding part of the scan.

Unfortunately the impression abutment is often covered by impression material or hardly surface above the impression. In yet another embodiment of the invention it is possible to mount a scan analog 1300 on the impression abutment. This analog is then scanned as a part of the impression scan and the known shape and dimensions can be applied to derive the corresponding implant position and orientation, e.g. using alignment of the CAD model or feature extraction. This operation can be performed for one or more implants combined or in an iterative procedure.

The prior art (U.S. Pat. No. 6,790,040) describes an alternative method based on encoded healing abutments (EHA) used to determine both the implant type and it's position and orientation from a scan.

In another embodiment of the invention it is for some cases also possible to scan an impression, or the positive poured model, of the implant directly and derive the position and orientation in a similar way as above.

In yet another embodiment, any of the above methods may be improved by including data from in-the mouth scanning.

Furthermore, it may also be possible to manufacture customized healing abutments based on the methods described above.

Manufacturing of the Model

If the dental laboratory or dentist would still need a traditional dental model e.g. to check or modify the fit and design of the manufactured restoration such model could still be manufactured from the impression scan. A traditional sectioned gypsum model is shown in FIG. 1A. The actually model manufacturing from the scan could be performed using classic manufacturing equipment or more suitable rapid prototype equipment such as milling machines or 3D printers. The model might be manufactured in any proper material such as plastic, polymers, wax, gypsum or ceramics.

The manufacturing equipment normally requires a solid 3D/watertight model to be created, see traditional model in FIG. 1A. Recall the impression scan 100 only contains a surface and not a solid model. To create an attractive model for the dental lab and dentist one or more of the following virtual steps need to be performed on the scan:

Inverting the surface from negative to positive
Cutting away extra surface (material)
Creating a virtual base
Trimming
Sectioning
Pinning or other positioning means
Add articulator interface
Add other structures e.g. implant/analog interface For achieving acceptance of the impression scanning technology it is very important to be able to manufacture models with similar performance as the gypsum models used in the dental labs today, e.g. a model where the teeth are on a base and the preparations are trimmed 1A00, sectioned 1A01 and pinned.

Figure 15:
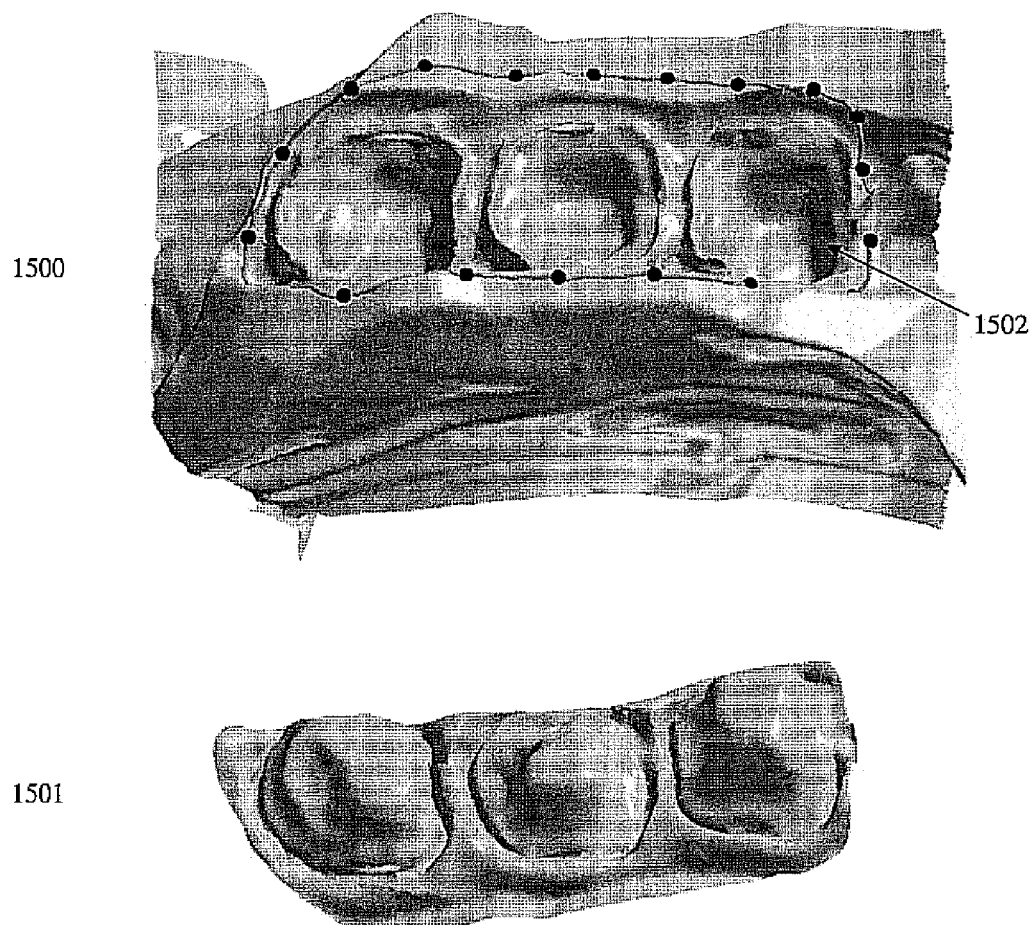

To transform the scan from an impression scan 1500 (negative) to a model 1501 (positive) the surface orientation need to be inverted. Preferably the scan should also be rotated, see FIG. 15. Typically the next step will then be to cut away part of the scan surface (material) that is not needed. The cutting can be performed by a splice based cutting tool 1502, triangle selections or other selection/cutting tools.

Figure 16:
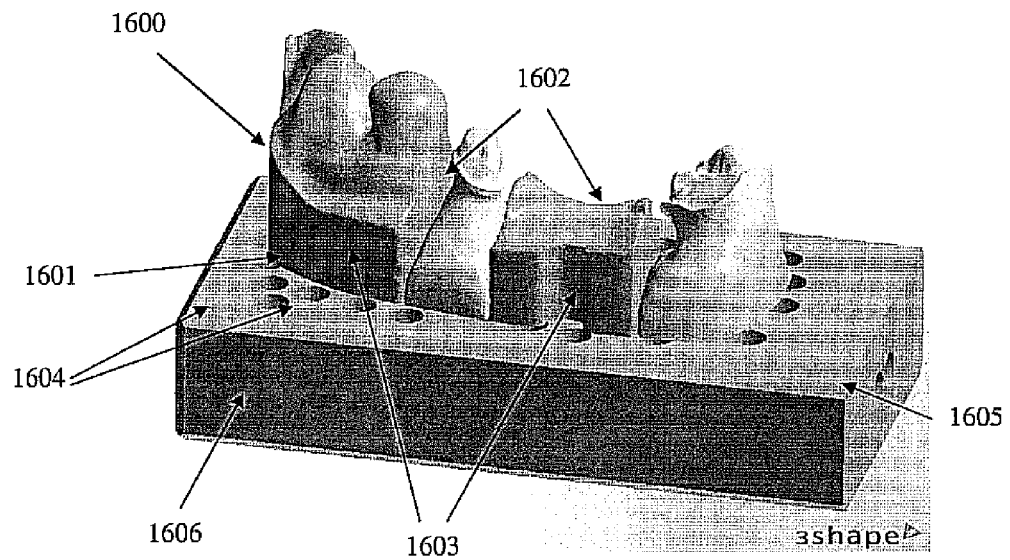
FIG. 16 Virtually model created model from impression scan with virtual base, trimming, sectioning, pinning and articulator interface.
Figure 17:
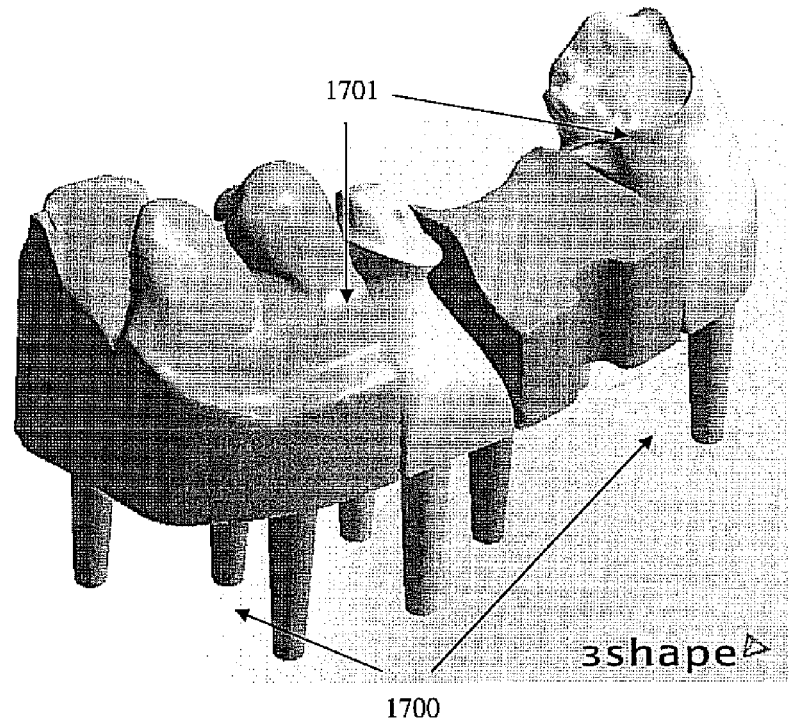
FIG. 17 Virtually created model with pins for positioning
FIG. 18 Virtually created model with more advanced sectioning and positioning means.
Figure 18:
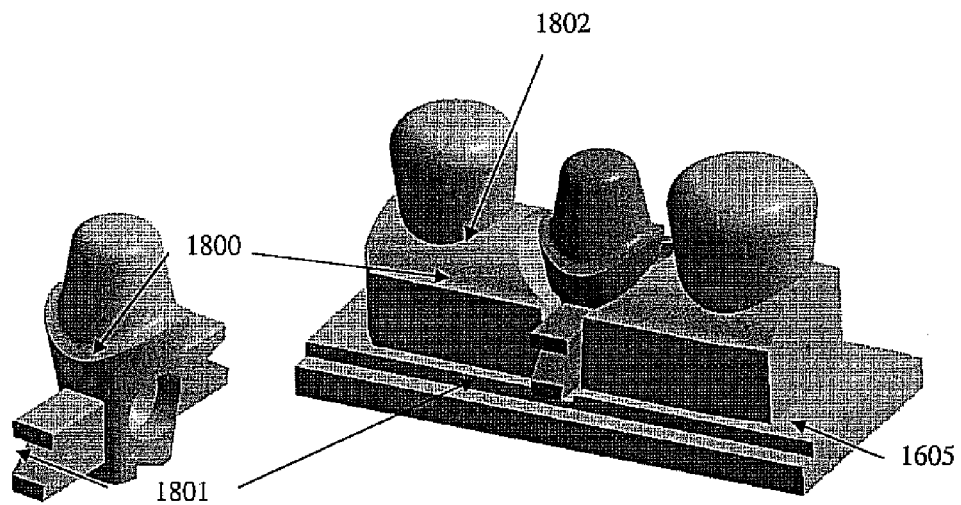

To create a basic solid model the cut scan surface can be attached or connected to a virtual base. The virtual base can be created by combining the scan surface with a base model e.g. by combing a CAD base with the scan surface by the creation of a connecting surface between the two surfaces. A variant of the process is illustrated in FIG. 16 where the cut scan surface 1600 is combined with a base 1601 that is created by vertically extending cut surface into a common surface, in this case a plane. The process is also shown in FIG. 9a to 9b and 10a to 10b. This may be perceived as forming a new base consisting of the material which is not positioned between two surfaces from the original scan.

For restoration purposes both the Maxilla (upper) and Mandible (lower) models need to be created. Recall the relative physical correct position is already known from the previous alignment.

An important extension to the virtual base is to add an articulator interface 1605 to the solid model such the manufactured models can be inserted and articulated in standard articulators. Optimal results would be obtained by using calibrated articulators. To minimise the manufacturing model cost it might be advantageous to insert a pre-manufactured interface 1606 between the model and the articulator.

As mentioned, the step of attaching a base is primarily carried out so that the cut scan surface will be a part of a solid shape which is required for a physical representation such as a manufactured model. Accordingly, one may subsequently cut part or all of the base from the solid shape either virtually or post manufacturing.

The trimming of the preparation is traditionally performed to remove the gingival and create accessibility to the margin line area for the crown design. Note for the traditional trimming of the preparation there is no information available that is not present in the impression. Hence the trimming can be performed virtually 1202 even improving the quality due to the controlled environment. The virtual trimming might be performed by selecting the area that is to be trimmed away on the model. One way to perform this selection is by placing a curve such as a spline on the surface part corresponding to the margin line. The trimming might then be performed by removing the surface outside of the margin line and making an artificial surface 1701, 1802 connecting the margin line to the rest of the model 1802 and/or preparation 1701. In many situations it is preferred to also manufacture a tooth crown and/or a prosthetic tooth, bridge or the like from the same model forming the basis for manufacturing the model. In this way booth may be manufactured from the three-dimensional model and the interaction may be physically investigated.

The sectioning of the model 1A01 typically into the individual preparations are performed to enable the dental technicians to easily access and work on the crowns, see FIG. 1a. An integrated part of the sectioning is the positing system so that the individual sections can be removed from the model and inserted back into the model preserving the original position. Typically the positioning means are pins attached to the sections and accurately fitting into the base. Other examples include screws, bolts, bores including or excluding threads, and push buttons. Preferably, positioning means are included in any of the sections resulting form the sectioning described below.

The virtual sectioning 1603 can replicate the classical sawed sectioning by the use of plane cuts as illustrated in FIG. 16. The pins 1700 can then be added and corresponding holes 1604 created using Boolean addition and subtract of CAD models. However the virtual approach enables the opportunity to create more advanced and optionally integrated sectioning and positioning means 1800 e.g. using Boolean functions. Due to the flexibility of the CAD design process almost any shape can be applied for sectioning and positioning such as cylindrical, triangles, spheres, cones 1800 or a combination of these 1800. Handles 1801 for easy removal and positioning can also be created e.g. using Boolean functions.

Figure 19:
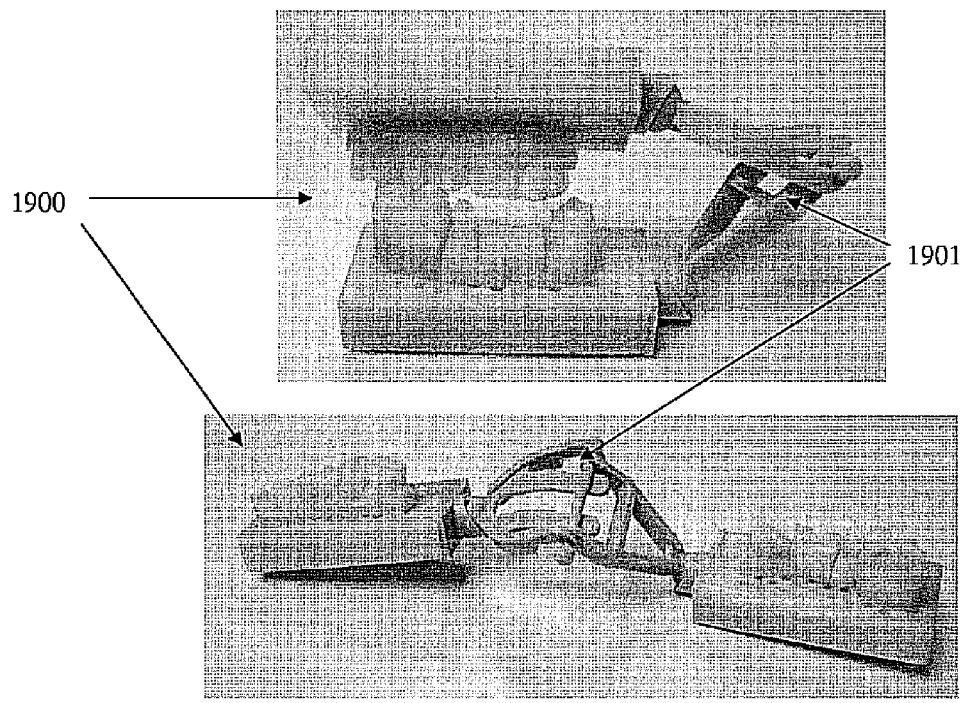

An example of a manufactured model 1900 mounted in a standard articulator 1901 is shown in FIG. 19. The model is manufactured using 3D printing.

Additional structures for dental items might also be added. This structure can be the full or partial dental item or interfaces to the dental item. One important example is printing the implant/analog directly as a part of the model, such that the designed structures e.g. customised abutment or super structure can be mounted directly on the model. For difficult implant structures or due to material requirements it might be preferable to add an interface for the implant/analog, such as a slot, so that the implant/analog can be mounted in the manufactured model afterwards. Examples on other dental items are attachments, locking systems other crown/bridge design support structures.

Although the text is relating to scans of dental impressions, it is clear for the person skilled in the art that the same methods and systems may be used for other types of scans of the mouth region such as traditional 3D scans of gypsum models, directly in the mouth scans, CT, MR or x-ray scans. Besides the manufacturing of parts or complete tooth crowns it may also be possible to manufacture customized healing abutments based on the methods described above.

REFERENCES

U.S. Pat. No. 6,579,095 (Mating parts scanning and registration methods).

Brian Curless and Marc Levoy, "Better optical triangulation through spacetime analysis", 1995 5th International Conference on Computer Vision, Boston, Mass., 20-23 Jun. 1995.

P. J. Besl and N. D. McKay, "A Method for Registration of 3-D Shapes", IEEE Trans. Pattern Anal. Machine Intell, February 1992 (Vol. 14, No. 2) pp. 239-256

The invention claimed is:

1. A method of obtaining orientation and localization of at least one dental implant, said method comprising:
   a. obtaining an impression comprising at least one impression abutment fixed to the impression, while the impression abutment is directly connected to said at least one dental implant(s)
   and/or
   obtaining an impression comprising at least one impression abutment fixed to the impression, while the impression abutment is directly connected to said at least one dental implant(s), and then mounting a scan analog on the impression abutment,
   b. obtaining pre-determined information of the shape of the impression abutment and/or scan analog, wherein the pre-determined information is a CAD model of the impression abutment and/or the scan analog,
   c. scanning at least a part of said impression, wherein said part comprises the at least one impression abutment and/or scan analog thereby obtaining scan data,
   d. determining the orientation and localization of the dental implant based on said pre-determined information and said scan data, where said determining comprises aligning the CAD of the impression abutment and/or the scan analog to the corresponding part of the scan data.

2. The method of claim 1, comprising obtaining a three-dimensional model based on the scan data.

3. The method of claim 1, wherein said determining the orientation and localization is furthermore based on one or more scans obtained by one or more of in-the mouth scanning, CT, MR or x-ray scans or a combination thereof.

4. A method of manufacturing a dental model of at least a part of an upper jaw and/or a lower jaw comprising:
   a. obtaining a three-dimensional model of at least the said part of the upper jaw and/or a lower jaw by either impression scanning, in-the mouth scanning, CT, MR or x-ray scans, scanning of a positive model or a combination thereof, wherein the said three-dimensional model is obtained by applying the method of claim 1,
   b. manufacturing a dental model from the obtained three-dimensional model.

5. The method of claim 4, wherein the dental model is manufactured by rapid prototyping equipment.

6. The method of claim 4, wherein the dental model is at least partially manufactured in plastic, polymers, wax, gypsum or ceramics.

7. The method of claim 4, comprising attaching the surface of the three-dimensional model to a base.

8. The method of claim 7, wherein said attachment is performed by vertically extending the surface to a common surface.

9. The method of claim 4, comprising obtaining a solid model from the three-dimensional model prior to manufacturing.

10. The method of claim 4, comprising sectioning the three-dimensional and/or solid model prior to manufacturing.

11. The method of claim 4, further comprising adding positioning means to the obtained model(s) prior to manufacturing.

12. The method of claim 4, wherein both the Maxilla and Mandible models are manufactured.

13. The method of claim 4, wherein at least one part of a tooth crown is manufactured based on the three-dimensional model.

14. The method of claim 4, further comprising the step of including at least one implant analog in the dental model.

15. The method of claim 14, wherein the position and orientation of said implant analog is found by the method of obtaining the localization and orientation of a dental implant according to claim 1.

16. A computer program product including a non-transitory computer readable medium, said computer readable medium having a computer program stored thereon, said program for obtaining orientation and localization of at least one dental implant comprising program code for conducting the method as defined in claim 1.

17. A system for obtaining orientation and localization of at least one dental implant, said system including a non-transitory computer readable memory having one or more computer instructions stored thereon, said instructions comprising Instructions for conducting the method as defined in claim 1.

* * * * *